United States Patent
Remon

(10) Patent No.: US 6,368,634 B1
(45) Date of Patent: *Apr. 9, 2002

(54) HIGH RELEASE SOLID PREPARATION, PREPARATION AND USE THEREOF

(75) Inventor: Jean Paul Remon, Ghent (BE)

(73) Assignee: Rijksuniversiteit Gent Laboratorium Voor Farmaceutishe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/537,793

(22) PCT Filed: Apr. 21, 1994

(86) PCT No.: PCT/BE94/00029

§ 371 Date: Feb. 27, 1996

§ 102(e) Date: Feb. 27, 1996

(87) PCT Pub. No.: WO94/23700

PCT Pub. Date: Oct. 27, 1994

(30) Foreign Application Priority Data

Apr. 22, 1993 (BE) .............................................. 9300407

(51) Int. Cl.⁷ ............................. A61K 9/50; A61K 9/14; A61K 9/16

(52) U.S. Cl. ....................... 424/501; 424/489; 424/490; 424/499

(58) Field of Search ................................ 424/468, 489, 424/419, 421, 422, 490, 499, 501

(56) References Cited

U.S. PATENT DOCUMENTS

| | | | |
|---|---|---|---|
| 3,689,500 A | * | 9/1972 | Bohner et al. ............... 424/421 |
| 4,904,699 A | * | 2/1990 | Bauer ......................... 514/972 |
| 5,283,065 A | | 2/1994 | Doyon et al. ............... 424/467 |
| 5,476,667 A | * | 12/1995 | Kristensen et al. ......... 424/489 |

FOREIGN PATENT DOCUMENTS

| | | |
|---|---|---|
| EP | 0249587 | * 12/1987 |
| EP | 0310999 | 4/1989 |

\* cited by examiner

Primary Examiner—Thurman K. Page
Assistant Examiner—Humera N. Sheikh
(74) Attorney, Agent, or Firm—Sughrue Mion, PLLC

(57) ABSTRACT

A solid preparation for a substantially immediate release of an active agent with low or very low solubility, which contains the active agent dissolved in a solubilizer, said dissolved active agent being contained in solid particles which are agglomerated into a system of agglomerated particles which is not a matrix or gelling forming agent.

38 Claims, 4 Drawing Sheets

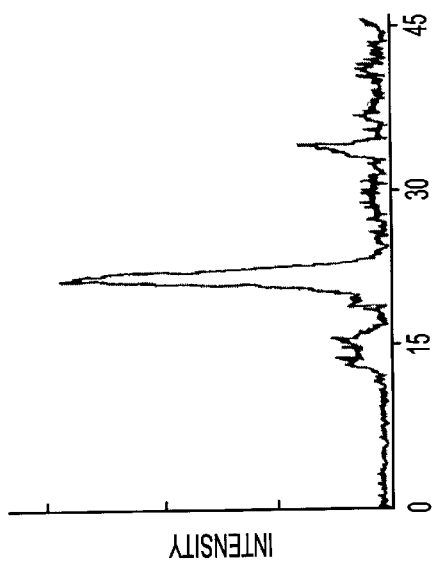
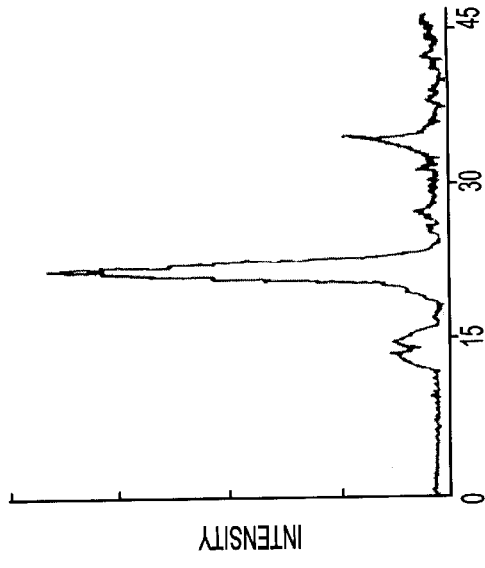
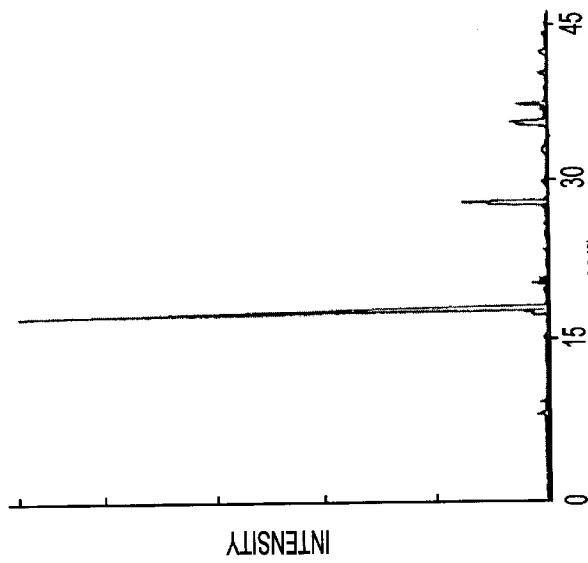

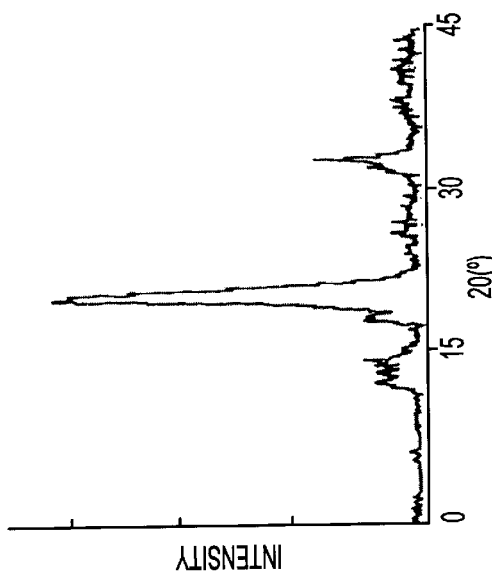
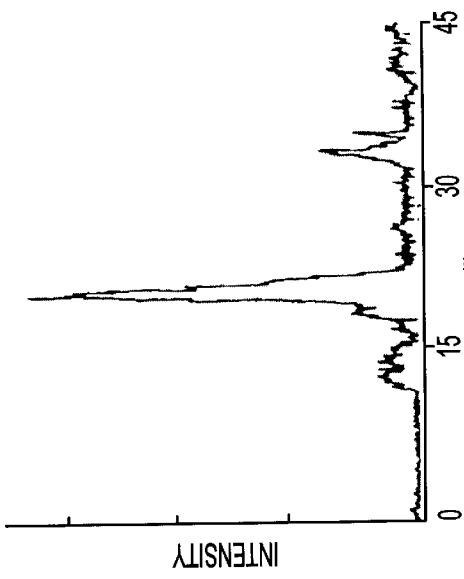
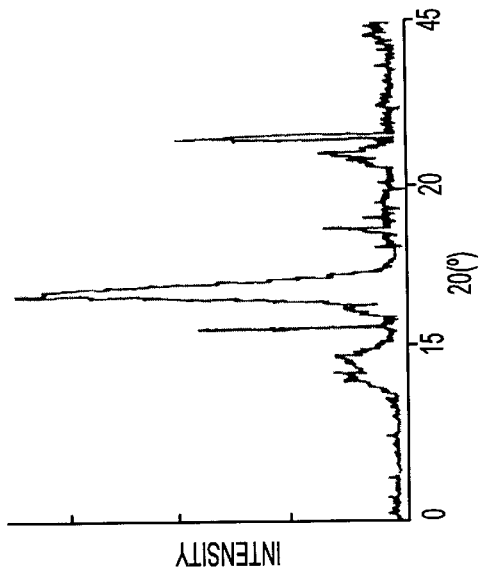

HIGH RELEASE SOLID PREPARATION, PREPARATION AND USE THEREOF

This application is a 371 of PCT/BE94/00029 Apr. 21, 1994

THE STATE OF THE ART

The present invention relates to a formulation of pellets or solid particles having a specific release, namely a very high release rate of active agents known as being poorly soluble.

In order to increase, the solubility or bioavailability of an active agent, it has been proposed to transform the active agent into its amorphous state. For example, U.S. Pat. No. 4,127,647 discloses the preparation of a solution of a macrolide, a solvent such as trichloroethane and chloroform, and a stabilizing substance such as hydroxypropylmethyl cellulose, and the spray drying of said solution at a temperature of 100–1300° C., whereby the solvent is evaporated and removed. The obtained amorphous product is thus free from solvent.

The skilled art worker did not make many attempts to produce pellets with a high release rate, as pellets are mainly produced in oral controlled dosage form.

The man skilled in the art has made searches and developments of pellets with slow or extended release properties.

For example, EP-A-0249587 teaches a solid pharmaceutical preparation with extended release properties, for compound having a very low solubility such as nifedipine and felodipine.

The preparation is obtained by dissolving felodipine or nifedipine in Cremophor® RH 60, and by mixing to the solution carriers such as a mixture containing hydroxypropylcellulose so as to form a hydrophilic gel matrix. The ratio active agent/solubilizer is in the range 1:1 to 1:10. In all the examples of preparations of EP-A-0249587, the active agent is contained into a matrix forming system, especially a gelling matrix.

BRIEF DESCRIPTION OF THE INVENTION

The present invention relates to a solid preparation suitable for a substantially immediate release of an active agent having a low or very low solubility. For example, the invention relates to a solid preparation for which more than 80% of the active agent is released within 2 hours, preferably within 1 hour or less from the administration.

The invention has especially as subject matter, a solid preparation obtained by pelletisation, i.e. an agglomeration process whereby fine powders or granules and excipients (non active materials) are shaped into fine, free-flowing spherical or non sperical units. Pellets are defined as dosage forms with a particle size above 250 $\mu$m.

The pellet consists of carriers, additives and active ingredients. The carrier can be a natural, a semi-synthetic or a synthetic polymer, but can also be of inorganic origin as for example talc, montmorillonites (as veegum, bentonites, etc. . . .) and other types of clay and phosphates as for example calcium phosphates. The active ingredient is preferably dissolved in a liquid phase (liquid as such or to be liquified by for example shear, temperature, etc. . . .) As liquid phase, the following ingredient can be described: oils (natural, synthetic, semi-synthetic), polar cosolvents (as polyethylene glycol, glycerol, propyleneglycol), fats and fat substituents and ionic, non ionic tensioactive agents of natural or synthetic origin. The active component can be a drug for human use, a drug for veterinary use, a chemical for application in the agrobusiness (fertilizers, pesticides and analogues), feed additives for human and animal use, etc.

The active ingredient is preferably mixed with the carrier as a solution in order to fix the liquid phase on the carrier. The mixing process of the liquid phase can be performed with different mixing techniques and granulation techniques such as planetary mixers, fluid-bed granulation, high shear mixers, etc. The pellets are then produced via extrusion-spheronisation, fluid-bed technology, rotary granulation, etc. . . .

The carrier can be water soluble or water insoluble and/or insoluble in the gastric medium and has advantageously the form of fine particles, preferably micro particles, for example particles having a diameter size of less than 500 $\mu$m.

When mixing the active ingedient and the carrier, or when agglomerating, other additives can be used, said additives having to be non gelling forming agents or having to be in such an amount that they are non gelling forming in water. Such additives can be water soluble or water dispersible.

The invention relates also to the manufacture of a solid dosage form, while the active ingredients are fixed in a liquid phase which is fixed on or in the carrier. An advantage of the invention lays in the preparation of pharmaceutical formulations for human or veterinary application whereby drugs with low solubility or slow dissolution rate can be formulated into a solid dosage releasing the drug quickly and presenting an enormous advantage in bioavailability. It also allows the handling of drugs and chemicals whereby toxicity and dust formation are providing problems during manipulation; the fixation of active ingredients as a liquid phase on a solid carrier can solve this problem.

The invention presents applications in the pharmaceutical area, food (human & animal) formulation, medicated feed, agrichemical, fixation of oils, fats and fatty , substituents in food processing, the transformation of liquid preparations into dry ones, the higher dissolution rate of active ingredients, etc. . . .

The solid preparation of the invention is a solid preparation which contains the active agent dissolved in a solubilizer, said dissolved active agent being contained in particles which are agglomerated in a system which is not a matrix forming system such as a gelling or gel forming system. The system of the invention is not a gel matrix nor a matrix which can form a gel in contact of water.

Preferably, the solubilizer is selected among the group consisting of oils, polar co-solvents, fats, tensioactive agents, solvents, fatty acids, fatty alcohols.

For example, the agglomerated particles or agglomeration of particles is free from compounds which are gel forming in water or in gastric medium or contains such a low amount of such compound that no water gelling effect exists. Compounds which have to be prevented to be used in the agglomeration of particles are for example hydrophylic gelling agent, hydroxypropylmethyl cellulose, compounds for forming an inert matrix, . . . .

The agglomeration contains preferably essentially micro particles, for example particles with a particle size below 500 $\mu$m. The agglomeration of particles contains advantageously more than 40%, even 50% by weight micro particles, such as insoluble particles, for example microcrystalline cellulose.

The agglomeration contains, in another embodiment, carboxymethylcellulose, salt thereof such as sodium carboxymethylcellulose or mixture thereof with microcrystalline cellulose.

The active agent is for example selected among the group consisting of hydrochlorothiazide, acetazolamide, acetylsalicylic acid, allopurinol, alprenolol, amiloride, antiarrhythmic, antibiotic, antidiabetic, antiepileptic, anticoagulants, antimycotic, atenolol, bendroflumethiazide, benzbromarone, benzthiazide, betamethasone, ester thereof, bronchodilator, buphenine, bupranolol, chemotherapeutic, chlordiazepoxide, chloroquine, chlorothiazide, chlorpromazine, chlortalidone, clenbuterol, clomipramine, clonidine, co-dergocrine, cortisone, ester thereof, dexamethasone, ester thereof, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxzolamide, fenoterol, fludrocortisone, ester thereof, fluphenazine, furorosemide, gallopamil, guanethidine, hormone, hydrochlorothiazide, hydrocortisone, ester thereof, hydroflumethiazide, immunosuppresive, ibuprofen, imipramine, indomethacine, coronartherapeutic, levodopa, salt of lithium, salt of magnesium, medroxyprogesteron acetate, menadione, methaqualone, 8-methoxypsoralen, methylclothiazide, methyldopa, methylprednisolone, methyltestosterone, methylthiouracil, methylxanthine, metipranolol, molsidomine, morphine, naproxen, nicergoline, nifedipine, norfenefrine, oxyphenbutazone, papaverine, parmathasone, ester thereof, pentobarbital, perphenazine, phenobarbital, phenylbutazone, phytomenadione, pirenzepine, polythiazide, prazosine, prednisolone, ester thereof, prednisone, ester thereof, probenecid, propranol, propylthiouracil, rescinnamine, reserpine, secbutabarbital, secobarbital, spironolactone, sulfasalazine, sulfonamide, thioridazine, triamcinolon, ester thereof, triamteren, trichlormethiazide, trifluoperazine, trifluopromazine, tuberculostatic, verapamil, virustatic, zytostatic, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen. Other active agents can also been used.

Preferred solubilizers are polyethyleneglycols, polyethyleneglycol derivatives such as esters or ethers, and mixture thereof.

The preparation which is solid has preferably the form of pellets, pellets which, if required, can be provided with a coating, for example an enteric coating. Such a coating is for example a coating disclosed in EP 0217778 (U.S. Pat. No. 4,832,958) or in EP 0153104, the content of which is incorporated by reference for describing examples of coating. While the weight ratio solubilizer/active agent is advantageously greater than 4, it has been observed that by using a ratio higher than 10 an atmost complete release of a drug could be reached in about 5–10 minutes. It has also been observed that when the weight ratio solubilizer/particles (carrier) was greater than 1:5, preferably 1:4, the release of drug was favorized. It seems that for such ratio the release of drug from the agglomerated particles is increased. Advantageously said ratio is greater than 1:3 or even 1:2.

The invention relates also to a process for the preparation of a solid preparation for a substantially immediate release of an active agent with a low or very low solubility, preparation which contains the active agent dissolved in a solubilizer, said dissolved active agent being contained in particles agglomerated into a system which is not a matrix forming system (such as a gel forming system or a gelling system).

According to a preferred process, the active agent is dissolved or suspended in a solubilizer so as to form a solution or supension, particles are mixed with the solution or supension, and agglomerated particles are formed.

Advantageously, the active agent is dissolved in a solubilizer, the quantity of which is such that the weight ratio solubilizer/active agent is greater than 4, preferably 10.

Preferably, the weight ratio solubilizer/particles is greater than 1:5, preferably greater than 1:4, most preferably 1:3, even 1:2.

The agglomeration of particles is made by means of any suitable liquid which do not contain a sufficient amount of gel forming agent or matrix forming agent and which preferably is free from gel forming agent or matrix forming agent. Such liquid is for example any liquid which can be evaporated after the agglomeration. Said liquid is preferably not the solubilizer of the active agent as such, but may contain such a solubilizer. Such a liquid can also contain other additives, for example water soluble additives. As typical agglomeration liquid, water can be used, said water being possibly mixed with water soluble additive(s) but non matrix forming and non gel forming and non gelling, water insoluble additives, solubilizer(s) of the active agent.

According to an embodiment of the processes of the invention, before being mixed with the active agent in a dry form or as a solution, the particles or carriers are treated with a solubilizer of the active agent, said solubilizer being or not the solubilizer used for treating the dry mixture particles-active agent or for preparing the solution of active agent. For example, the previously treated particles contain 5 or 10% solubilizer(s) of the active agent. However, the ratio solubilizer/particles (w/w) is advantageouly greater than 1:5.

As it was observed that very high release of drug could be reached when using such ratio solubilizer/particles, the invention relates also to a mixture of particles, such as water insoluble particles, containing a solubilizer selected among the group consisting of oils, polar co-solvents, fats, tensioactive agents, solvents, fatty acids, fatty alcohols, the weight ratio solubilizer/particles being greater than 1:5, preferably 1:4, most preferably 1:3 or even 1:2.

Advantageously, the particles are micro particles, such microcrystalline cellulose.

Such a mixture is suitable as agent for favorizing the release or bioavailability of an active agent from pellets or from agglomerated particles. The invention relates thus also to the use of such a mixture for the preparation of solid formulation with increased or improved release or bioavailability of an active agent.

Furthermore, it has been observed that when heating a preparation containing a drug and a suitable solubilizer of said drug, preferably a preparation according to the invention, the bioavailability of the drug was increased and the release of the drug was still increased. For example, such a heat treatment is a treatment at a temperature from 40° C. up to the boiling point of the solubilizer, preferably at a temperature from 40° C. to 60° C., during at least 3 hours, preferably during at least 24 hours.

DESCRIPTION OF THE DRAWING

FIGS. 6A, 6B and 6C give the X-ray diffraction patterns of respectively pure hydrochlorothiazide, pure microcrystalline cellulose (Avicel PH101) and microcrystalline cellulose pellets containing 3.5% hydrochlorothiazide, and 32% solubilizer (PEG 400), and FIGS. 7A, 7B and 7C give the X-ray diffraction patterns of microcrystalline cellulose pellets containing 3.5% hydrochlorothiazide and 21% solubilizer (Cremophor) respectively after preparation, after 6 months storage period at 25° C. and after a thermal, treatment at 450° C. during 96 hours.

DESCRIPTION OF PREPARATIONS

EXAMPLE 1

5 g Nifedipine has been dissolved in 95 g of a polyethyleneglycol derivative (PEG-7 glyceryl cocoaat sold by Henkel, Düsseldorf, Germany under the trade name CETIOL HE®) at a temperature higher than 40° C., for example 50° C., but at a temperature lower than the boiling point thereof.

When the Nifedipine was completely dissolved the solution was mixed with 375 g water (demineralized) and was then mixed with 375 g microcrystalline cellulose (Avicel PH 101, FMC, Cork, Ireland) in a, planetary mixer.

The so obtained mixture was then extruded in an extruder and spheronised in a spheronizer (Model 15, Caleva Ltd., Dorset, U.K.) during 10 minutes at 750 rpm.

Thereafter, the pellets were dried in a fluidized bed dryer at 50° C. during 20 minutes so as to obtain pellets having a moisture content of less than 2%.

The dissolution of the so formed pellets was measured as follows 1 g pellet sample (diameter size 710–100 μm) was added to 900 ml water having a temperature of 37° C. The mixture was agitated (75 rpm). The method used was conform to the paddle method as described in USP XXII. The extinction was continuously monitored at 3320 nm using a Zeiss PM6-UV spectrophotometer (Zeiss, Oberkochen, Germany).

Figure 1:
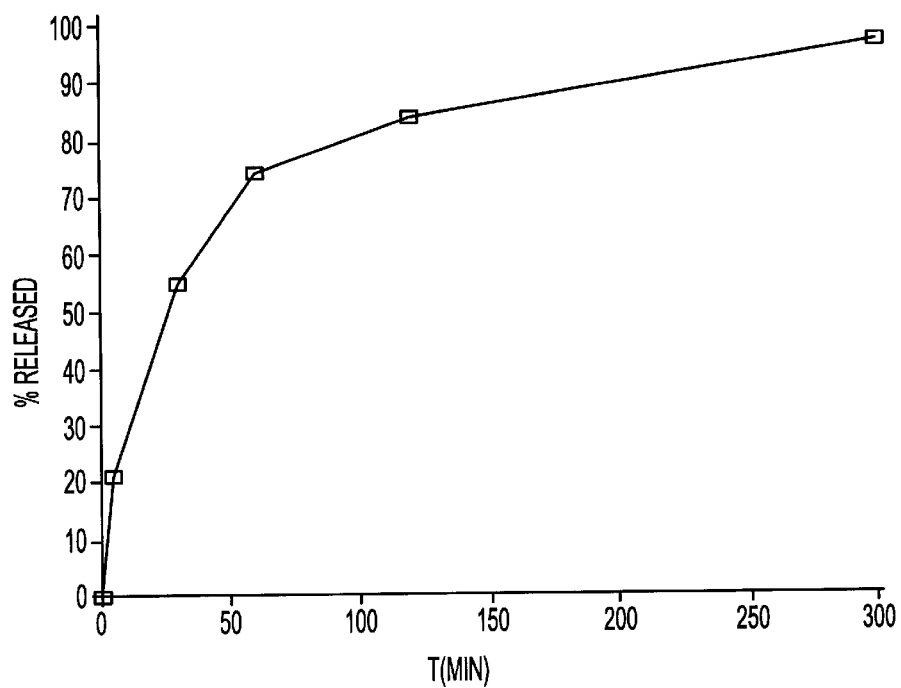
FIG. 1 shows the dissolution of Nifedipine contained in pellets (1% Nifedipine –19% solubilizer)

The dissolution of the pellet is shown in FIG. 1. It appears from said figure that more than 50% of the active ingredient was released within 1 hour.

EXAMPLE 2

25 g Indomethacine has been dispersed and dissolved in 100 g of a polyethyleneglycol derivative (PEG-7 glyceryl cocoaat sold by Henkel, Düsseldorf, Germany under the trade name CETIOL HE®) at a temperature higher than 40° C., for example 50° C., but at a temperature lower than the boiling point thereof.

400 g water was then added to the indomethacine solution. The so obtained mixture was then mixed with 375 g microcrystalline cellulose (Avicel PH 101, FMC, Cork, Ireland) in a planetary mixer, and then the so obtained mixture was then extruded in an extruder and spheronised in a spheronizer (Model 15, Caleva Ltd., Dorset, U.K.) during 10 minutes at 750 rpm.

Thereafter, the pellets-were dried in a fluidized bed dryer at 50° C. during 20 minutes so as to obtain pellets having a moisture content of less than 2%.

Figure 2:
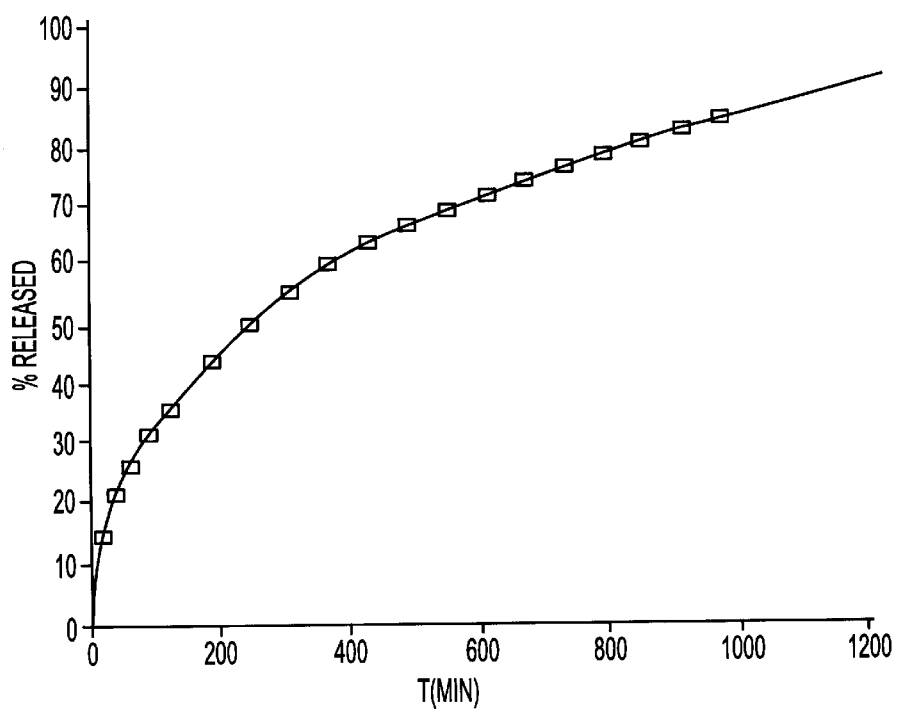
FIG. 2 shows the dissolution of Indomethacine contained in pellets (2% Indomethacine –20% solubilizer)

The dissolution of 1 g pellet (710–100 μm) was measured as for example 1 and is shown in FIG. 2.

It appears from said Figure that about 40% of the active agent was dissolved within 2 hours.

EXAMPLES 3 and 4

Hydrochlorothiazide (HCT) (Batch no 5327B; Ludeco, Brussels, Belgium) was used as drug in these examples. This diuretic drug is practically insoluble in water (25° C.) and has a solubility of 250 mg/L in 0.1 N HCl (25° C.). Polyethylene glycol 400 (PEG 400) (α Pharma, Vichte, Belgium) and PEG 40 hydrogenated castor oil (Cremophor® RH40) (BASF, Ludwigshafen, Germany) were used as solubilising agents. Microcrystalline cellulose (A (Avicel® PH 101) (FMC Wallington, Little Island, Cork, Ireland) was taken as a filler and the pellet forming material. Demineralised water was used as granulation liquid, next to the solubilising agents.

Pellets containing 2,11,21 and 32% (w/w) polyethylene glycol 400 and 7,14 and 21% (w/w) Cremophor® RH40 were prepared. All formulations contained 3.5% (w/w) of hydrochorothiazide. The remaining part of all formulations -consisted of Avicel® PH101. For each composition the amount of water was adjusted to get the proper plasticity of the mass. A reference formulation was prepared containing 3.5% (w/w) hydrochlorothiazide and Avicel® PH101 as a filler, without solubilising agent.

Microcrystalline cellulose and hydrochlorothiazide were mixed for 10 minutes at 60 rpm in a planetary mixer (Kenwood Chef, Hampshire, UK). The granulation liquid was prepared by mixing the dissolution enhancer, PEG 400, or the Cremophor® RH40 heated at 450° C., and demineralised water (heated at 450° C. in the case of Cremophor® RH40). The Cremophor® RH40/water mixture was cooled to room temperature under continuous stirring. Next, the granulation liquid was added to the powder mix and granulated for 10 minutes at 60 rpm in a planetary mixer (Kenwood Chef, Hampshire, UK). The granulated mass was extruded at 40 rpm using a basket extruder (Caleva Model 10, Caleva Ltd., Sturminster Newton, Dorset, UK) through a screen with a thickness of 1 mm and die perforations of 1 mm diameter. 135 g of the extrudate was spheronised for 5 minutes at 750 rpm in a Caleva Model 15 spheroniser (Caleva Ltd., Sturminster Newton, Dorset, UK). The resulting pellets were dried for 12 hours in a ventilated oven (Herauws, Obendorf, Germany) at 30° C., after which the dried pellets were sieved using a nest of sieves of 710,1000 and 1400 μm vibrated on a sieve shaker (Rheostat, Willemshaven, Germany) at maximum vibrational speed. A second preparation method was used for PEG 400 pellets containing 32% PEG 400 and 3.5% hydrochlorothiazide (HCT). HCT was first dissolved in the amount of PEG 400 available. This solution was added to the demineralised water, next the complete liquid mixture was added to the microcrystalline cellulose and further processed as in the method described herebefore. All formulations were stored under ambient conditions during a period of 6 months. Half of the bath formulated with 21% (w/w) Cremophor® RH40 and 3.5% (w/w) HCT received a thermal treatment for 96 hours at 45° C.

Dissolution testing was performed on 700 mg pellets (710–100 μm fraction) containing 25 mg hydrochlorothiazide in 0.1N HCl (37° C.) using the paddle method (USP XXII) at a rotational speed of 100 rpm. Samples of 5 ml were withdrawn at time $t_i$ (i=0,2,5,10,15,20,30,45,60,75 and 90 minutes) and replaced with an equal amount of test medium. The samples were filtered through a porous metallic filter (pore diameter: 2 μm) and spectrophotometrically analyzed at 273 nm with a ZEISS-spectrophotometer (ZEISS PMG-UV, Oberkochen, Germany). Each formulation was tested four times. The percentage of hydrochlorothiazide released from the formulation at time was calculated and corrected for the amount of HCT withdrawn at time $t_{i-1}$. After a 6 months storage period under ambient conditions the dissolution tests were repeated in order to check stability of the pellets formulations. X-ray diffraction patterns were taken of the formulations containing 11 and 32% (w/w) PEG 400 and the formulations containing 21% (w/w) Cremophor® RH40 immediately after preparation, after thermal treatment and after 6 months storage under ambient conditions.

Figure 3:
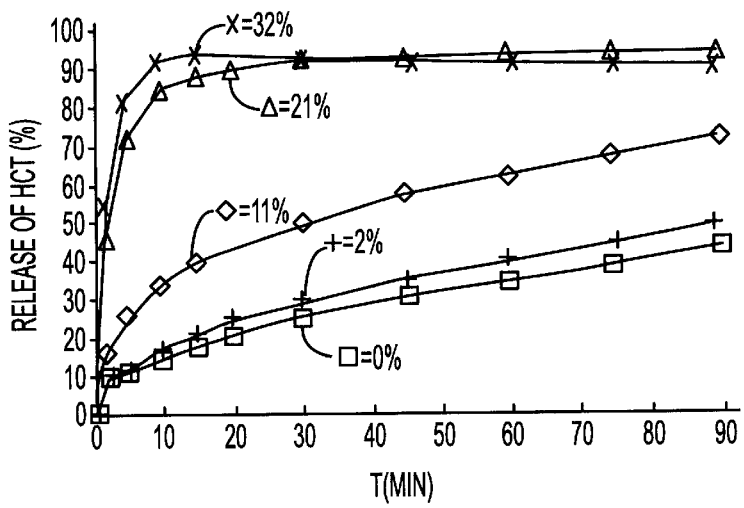
FIG. 3 shows the dissolution of hydrochlorothiazide contained in pellets containing 3.5% hydrochlorothiazide and from 2 to 32% solubilizer (PEG), after preparation (□: 0% solubilizer; +: 2% solubilizer, ◊: 11% solubilizer; Δ: 21% solubilizer and X: 32% solubilizer)

During preliminary experiments the maximum amount of PEG 400 that could be incorporated in the Avicel® PH101-pellets was determined to be 43% (w/w). At this concentration of PEG 400, pellets sticked to each other, whereas below this concentration the pellets still has their typical free-flowing capacity. The limit of Cremophor® RH40 concentration that could be incorporated in the pellets was 21% (w/w). Increasing the concentration of Cremophor® RH40 in the pellets caused the hardness of the pellets to drop below an acceptable level. The in-vitro dissolution profiles of the formulations containing PEG 400 are shown in FIG. 3. Pellets containing 21 and 32% (w/w) PEG 400 released more than 70 and 80% of the active ingredient within the first minutes, respectively. This means a drastic increase in the in-vitro release rate compared to the reference pellets releasing 10 and 45% of HCT after 5 and 90 minutes, respectively. No differences between the in-vitro dissolution profiles were obtained from pellets prepared by both methods. The typical X-ray diffraction pattern of crystalline HCT in the pellets containing 32% (w/w) PEG 400 could not be detected (FIG. 6) showing that the drug was dissolved and said dissolved drug was contained in microcrystalline cellulose. When reducing the percentage of PEG 400 in the formulation to 11 and 2% (w/w), the in-vitro drug release rate was lowered to 26% and 11% after 5 minutes, respectively (FIG. 3). The in-vitro release rate of HCT from the formulation containing 2% (w/w) PEG 400 was very similar to the reference pellets. A solubility test of HCT in PEG 400 at room temperature showed that only a fraction of the amount HCT present could dissolve in the 2% PEG 400 formulation. Although the solubility test showed that all the HCT could dissolve in the PEG 400 present in the formulation containing 11% (w/w) PEG 400, the in-vitro release rate however dropped compared to the formulation containing 21% (w/w) PEG 400. The X-ray diffraction patterns of the pellets containing 11% of PEG 400 showed no difference with the patterns of the pellets containing 32% of PEG 400 (FIG. 6) indicating that all HCT was dissolved in PEG 400. This shows clearly that the solubilizer has an influence on the microcrystalline cellulose particle, i.e. that when using sufficient solubilizer, the solubilizer increases the release of the drug. This clearly shows that the use of particles containing solubilizer, for example only solubilizer, increase the release of the drug and act as agent for increasing the release or bioavailability of the drug.

Figure 4:
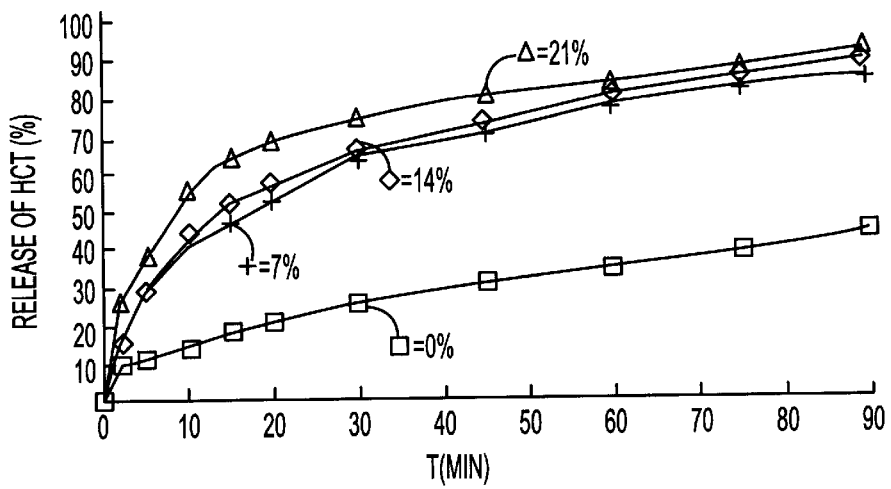
FIG. 4 shows the dissolution of hydrochlorothiazide contained in pellets containing 3.5% hydrochlorothiazide and from 0 to 21% solubilizer (Cremophor), after preparation (□: 0% solubilizer; +: 7% solubilizer; ◊: 14% solubilizer, and Δ: 21% solubilizer)
Figure 5:
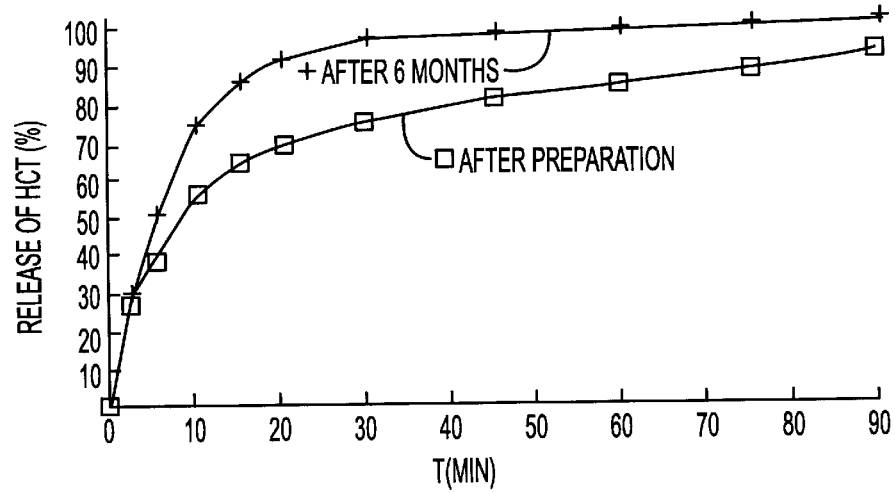
FIG. 5 shows the dissolution profiles of pellets containing 3.5% hydrochlorothiazide and 21% solubilizer (Cremophor) immediately after preparation (□) and after a 6 months storage period at 250 C. (+)

Storage of the PEG 400-pellets under ambient conditions for a period of 6 months did not alter the dissolution profile of HCT. FIG. 4 shows the dissolution profiles of the pellets containing 0,7,14 and 21% (w/w) Cremophor® RH40. An increase in the in-vitro release rate of HCT from the Avicel® PH101-pellets was seen, although not as pronounced compared to the use of 32% (w/w) PEG 400. The X-ray diffraction pattern of the formulation containing 21% (w/w) of Cremophor® RH40 showed the presence of some HCT-crystals in the formulation (FIG. 7), indicating that only part of the HCT was in solubilized form in the pellets. The dissolution profiles of pellets containing 21% of Cremophor® RH40 showed an increase of the in-vitro release rate after storage under ambient conditions (25° C.) during a time period of 6 months (FIG. 5). The same increase of the in-vitro release rate was seen after the thermal treatment of the pellets at 45° C. for 96 hours. This increase is due to an increase of the amount of HCT solubilised in the Cremophor® RH40. This hypothesis was is confirmed by X-ray diffraction patterns showing that no crystalline HCT could be detected after a storage period of 6 months under ambient conditions (25° C.) (FIG. 7B), nor after a thermal treatment at 45° C. during 96 hours (FIG. 7C). Although all HCT was solubilised in Cremophor® RH40 the release rate of HCT did not reach the release rate of the pellets formulated with 32% (w/w) PEG 400.

EXAMPLE 5

2,5 g alprenolol and 10 g hydrochlorothiazide have been dry mixed for 10 minutes at 60 rpm in a planetary mixer (Kenwood Chef, Hampshire, UK).

The mixture has then been mixed with 50 g PEG-800 at 50° C. so as to obtain a solution of alprenolol and hydrochlorothiazide.

95 g water was then added to the solution and the so obtained solution was mixed with 125 g microcrystalline cellulose (Avicel PH 101) in a planetary mixer.

The mixture was then extruded, spheronized and dried as described in example 1.

EXAMPLE 6

6.1 Preparation of Granules of Microcrystalline Cellulose and PEG-400

A granulation liquid was prepared by mixing 100 g polyethyleneglycol (PEG-7 glyceryl cocoaat—CETIOL HE®) and 375 g water.

375 g microcrystalline cellulose Avicel PH 101 was mixed with the granulation liquid and granulated for 10 minutes at 60 rpm in a planetary mixer. (Kenwood Chef, Hampshire, UK).

6.2 Preparation of Granules of Microcrystalline Cellulose, Lactose, PEG-400 and HCT A solution has been prepared by mixing 100 g PEG-400 (CETIOL HE®), 10 g lactose, 20 g HCT and 375 g water.

300 g microcrystalline cellulose Avicel PH 101 was mixed with the above mentioned solution, and granulated as explained in point 6.1.

6.3 Preparation of Pellets 100 g of granules of Avicel-PEG 400 were mixed with 200 g of granules of Avicel-HCT-PEG 400. The mixture was extruded at 40 rpm using a basket extruder (Caleva Model 10, Caleva Ltd., Sturminster Newton, Dorset, UK) through a screen with a thickness of 1 mm diameter. The extrudate was then spheronized for 5 minutes at 750 rpm in a Caleva Model 15 spheronizer and the resulting pellets were dried for 12 hours in a ventilated oven at 30° C.

The pellets contained:

2.5% HCT 1.2% Lactose

74% Avicel (microcrystalline cellulose)

22.3 a PEG-400

6.4 Pellets were Prepared by Using Only Granules of the Preparation 6.2

The so obtained pellets had a good release of drug in water, however said release was no so excellent as the release of the pellets of the preparation 6.3.

EXAMPLE 7

Pellets containing 3.5% Hydrochlorothiazide (HCT) and 30% Polyethylene glycol PEG 400 have been prepared as follows:

A solution of hydrochlorothiazide has been prepared by mixing 35% HCT with 150 g PEG 400 and 300 g water at 50° C.

675 g of microcrystalline cellulose Avicel PH101 was mixed with 150 g PEG 400 in a planetary mixer for 10 minutes. Particles containing PEG 400 were so obtained.

The so obtained particles were then mixed with the solution of HCT in a planetary mixer so as to obtain a granulated mass. Said mass was then transformed into pellets in a manner similar to that disclosed for examples 3 and 4.

A previous treatment of the carrier with the solubilizer seems to be suitable for having an excellent release, showing a further possible use of the mixture particles according to the invention.

EXAMPLE 8

Pellets containing 3.5% hydrochlorothiazide, 23% Polyethylene glycol PEG 400 and 10% Cremophor RH40 have been prepared as follows:

A solution of hydrochlorothiazide has been prepared by mixing 35 g HCT with 150 g Cremophor RH 40 and 80 g PEG 400 in a planetary mixer for 10 minutes. Particles containing Cremophor RH 40 and PEG 400 were so obtained.

The so obtained particles were then mixed with the solution of HCT in a planetary mixer so as to obtain a granulated mass. Said mass was then transformed into pellets in a manner similar to that disclosed for examples 3 and 4.

EXAMPLE 9

Pellets containing various active agents have been prepared as described in example 1, but by using various amounts of water "W", microcrystalline cellulose (Avicel PH 101) "MC", and "PEG" (Cetiol HE) or/and Cremophor RH40 "C". Said amounts are given in the following table.

TABLE

| ACTIVE AGENT | W | MC | C | PEG |
|---|---|---|---|---|
| 5 g Nifedipine | 375 g | 375 g | 0 g | 150 g |
| 5 g Nifedipine | 375 g | 300 g | 75 g | 25 g |
| 10 g Ibuprofen | 375 g | 300 g | 0 g | 100 g |
| 10 g Diclofenac | 375 g | 300 g | 0 g | 100 g |
| 5 g Cimetidine | 275 g | 0 g | 100 g | 0 g |

What is claimed is:

1. Solid pharmaceutical preparation for oral administration for a substantially immediate release of an active agent with a low solubility, said preparation containing:
   (a) the active agent, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3);
   (b) said pharmaceutically acceptable solubilizer as the only solubilizer present for forming a solution in which the active agent is dissolved, and
   (c) solid polymeric or inorganic particles on which said solution is fixed, said particles containing said solution being agglomerated in an agglomerate which is not a matrix or gel containing matrix or gel forming components which can cause the solid preparation to gel in water or in gastric medium.

2. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said preparation containing:
   (a) a liquid solution in which the active agent is dissolved in the solubilizer, and
   (b) a carrier consisting of an agglomeration of solid polymeric or inorganic particles, said liquid solution being fixed on or in the carrier, said method comprising:
     dissolving the active agent in said solubilizer as the only solubilizer present so as to form said liquid solution;
     mixing said solid polymeric or inorganic particles with the liquid solution so as to form a composition of solid particles containing said liquid solution;
     agglomerating the composition in the absence of matrix or gel forming components which can cause the pellet to gel in water or gastric medium so as to form an agglomerate of solid particles containing said liquid solution;
     heat treating the solid particles of the system at a temperature between 40° C. and the boiling point of the solubilizer;
     and spheronizing the heat treated agglomerate,
       thereby forming pellets wherein the active ingredient is capable of substantially immediate release.

3. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said pellet containing:

(a) the active agent, (b) said liquid pharmaceutically acceptable solubilizer for forming a liquid solution in which the active agent is dissolved, and (c) solid pharmaceutically acceptable microcyrstalline cellulose particles on which said liquid solution is fixed, said solid particles containing said liquid solution being agglomerated in the absence of matrix or gel forming components which can cause the pellet to gel in water or in gastric medium, said process comprising:

mixing together the active agent, the solid microcrystalline cellulose particles and the solubilizer as the only solubilizer present, so as to form a liquid solution of the active agent contained in the solid particles, agglomerating the solid particles containing the liquid solution of active agent in the absence of said matrix and gel forming components to form an agglomerate which is not a matrix or gel, heat treating said liquid agglomerate containing the solution of active agent at a temperature between 40° C. and the boiling point of solubilizer, and spheronizing the heat treated agglomerate, thereby forming pellets wherein the active ingredient is capable of substantially immediate release.

4. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said pellet containing:

(a) the active agent, (b) said liquid pharmaceutically acceptable solubilizer for forming a liquid solution in which the active agent is dissolved, and (c) solid pharmaceutically acceptable particles on which said liquid solution is fixed, said solid particles containing said liquid solution being agglomerated in a system which is not a matrix or gel forming system containing matrix or gel forming components which can cause the pellet to gel in water or in gastric medium, said process comprising:

mixing together solid microcrystalline cellulose particles and the active agent in powder form, mixing the so obtained mixture with the solubilizer, as the only solubilizer present, agglomerating the solid particles containing the liquid solution of active agent in the absence of said matrix and gelling forming components to form an agglomerate which is not a matrix or gel, heat treating the agglomerate containing the liquid solution of active agent at a temperature between 40° C. and the boiling point of the solubilizer, and spheronizing the heat treated agglomerate, thereby forming pellets wherein the active ingredient is capable of substantially immediate release.

5. Solid pharmaceutical preparation for oral administration for a substantially immediate release of an active agent with a low solubility, said preparation containing:

(a) the active agent, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3);

(b) said pharmaceutically acceptable solubilizer as the only solubilizer present for forming a solution in which the active agent is dissolved, and (c) solid microcrystalline cellulose particles on which said solution is fixed, said particles containing said solution being agglomerated in an agglomerate which is not a matrix or gel containing matrix or gel forming components which can cause the solid preparation to gel in water or in gastric medium.

6. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said preparation containing:

(a) a liquid solution in which the active agent is dissolved in the solubilizer, and (b) a carrier consisting of an agglomeration of solid microcrystalline cellulose particles, said liquid solution being fixed on or in the carrier, said method comprising:

dissolving the active agent in said solubilizer as the only solubilizer present so as to form said liquid solution;

mixing said solid microcrystalline cellulose particles with the liquid solution so as to form a composition of solid particles containing said liquid solution;

agglomerating the composition in the absence of matrix or gel forming components which can cause the pellet to gel in water or gastric medium so as to form an agglomerate of solid particles containing said liquid solution;

heat treating the solid particles of the system at a temperature between 40° C. and the boiling point of the solubilizer;

and spheronizing the heat treated agglomerate, thereby forming pellets wherein the active ingredient is capable of substantially immediate release.

7. The pellet of claim 1, in which the system of agglomerated particles contains micro particles.

8. The preparation of claim 1, in which at least 50% by weight of the system of agglomerated particles consists of micro particles.

9. The pellet of claim 1, in which the active agent is selected from the group consisting of hydrochlorothiazide, acetazolamide, acetylsalicylic acid, allopurinol, alprenolol, amiloride, antiarrhythmic, antibiotic, antidiabetic, antiepileptic, anticoagulants, antimycotic, atenolol, bendroflumethiazide, benzbromarone, benzthiazide, betamethasone, ester thereof, bronchodilator, buphenine, bupranolol, chemotherapeutic, chlordiazepoxide, chloroquine, chlorothiazide, chlorpromazine, chlortalidone, clenbuterol, clomipramine, clonidine, co-dergocrine, cortisone, ester thereof, dexamethasone, ester thereof, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxzolamide, fenoterol, fludrocortisone, ester thereof, fluphenazine, furorosemide, gallopamil, guanethidine, hormone, hydrochlorothiazide, hydrocortisone, ester thereof, hydroflumethiazide, immunosuppresive agents, ibuprofen, imipramine, indomethacine, coronartherapeutic, levodopa, salt of lithium, salt of magnesium, medroxyprogesteron acetate, menadione, methaqualone, 8-methoxypsoralen, methylclothiazide, methyldopa, methylprednisolone, methyltestosterone, methylthiouracil, methylxanthine, metipranolol, molsidomin, morphine, naproxen, nicergoline, nifedipine, norfenefrine, oxyphenbutazone, papaverine, parmathasone, ester thereof, pentobarbital, perphenazine, phenobarbital, phenylbutazone, phytomenadione, pirenzepine, polythiazide, prazosine, prednisolone, ester thereof, prednisone, ester thereof, probenecid, propranolol, propylthiouracil, rescinnamine, reserpine, secbutabarbital, secobarbital, spironolactone, sulfasalazine, sulfonamide, thioridazine, triamcinolon, ester thereof, triamteren, trichlormethiazide, trifluoperazine, trifluopromazine, tuberculostatic, verapamil, virustacic, zytostatic, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen.

10. The pellet claim 1, which is provided with an enteric coating.

11. The pellet claim 1, in which the weight ratio solubilizer/active agent is at least.

12. The pellet of claim 1, in which the weight ratio solubilizer/solid polymeric or inorganic particles is greater than 1:5.

13. The pellet of claim 1, in which the weight ratio solubilizer/solid polymeric or inorganic particles is greater than 1:3.

14. Process of claim 2, in which the active agent is dissolved in a solubilizer, the quantity of which is such that the weight ratio solubilizer/active agent is greater than 4.

15. Process of claim 2, in which the weight ratio solubilizer/particles is greater than 1:5.

16. Process of claim 2, in which the weight ratio solubilizer/particles is greater than 1:3.

17. Process of claim 2, in which the particles are heat treated at a temperature comprised between 40° C. and 60° C.

18. Process of claim 2, in which after the agglomeration of the particles, the particles are heated at a temperature higher than 40° C. during at least 3 hours.

19. The pellet of claim 1, in which the weight ratio solubilizer/active agent is greater than 10.

20. The pellet of claim 1, in which the weight ratio solubilizer/solid polymeric or inorganic particles is greater than 1:4.

21. The pellet of claim 1, in which the weight ratio solubilizer/solid polymeric or inorganic particles is greater than 1:2.

22. Process of claim 2, in which the particles are heat treated at a temperature between 40° C. and 60° C.

23. Process of claim 2, in which after the agglomeration of the particles, the particles are heated at a temperature higher than 40° C. for at least 3 hours.

24. Process of claim 2, in which after the agglomeration of the particles, the particles are heated at a temperature of 40° C. to 60° C. for at least 3 hours.

25. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said pellet containing:

(a) the active agent, (b) said liquid pharmaceutically acceptable solubilizer for forming a liquid solution in which the active agent is dissolved, and (c) solid pharmaceutically acceptable polymeric or inorganic particles on which said liquid solution is fixed, said solid particles containing said liquid solution being agglomerated in the absence of matrix or gel forming components which can cause the pellet to gel in water or in gastric medium, said process comprising:

mixing together the active agent, the solid polymeric or inorganic particles and the solubilizer as the only solubilizer present, so as to form a liquid solution of the active agent contained in the solid particles, agglomerating the solid particles containing the liquid solution of active agent in the absence of said matrix and gel forming components to form an agglomerate which is not a matrix or gel, heat treating said liquid agglomerate containing the solution of active agent at a temperature between 40° C. and the boiling point of solubilizer, and spheronizing the heat treated agglomerate, thereby forming pellets wherein the active ingredient is capable of substantially immediate release.

26. Process of claim 25, wherein the weight ratio solubilizer/active agent is greater than 4.

27. Process of claim 25, in which the weight ratio solubilizer/particles is greater than 1:5.

28. Process of claim 25, in which the weight ratio solubilizer/particles is greater than 1:3.

29. Process of claim 25, in which the particles are heat treated at a temperature between 40° C. and 60° C.

30. Process of claim 25, in which after the agglomeration of the particles, the particles are heated at a temperature higher than 40° C. for at least 3 hours.

31. Process for the preparation of an oral pellet for a substantially immediate release of an active agent with a low solubility, said active agent dissolving in a liquid pharmaceutically acceptable solubilizer selected from the group consisting of (1) polyethyleneglycol, (2) polyethyleneglycol hydrogenated castor oil, (3) a mixture of polyethyleneglycol and polyethelenglycol hydrogenated castor oil and a (4) a mixture of water with (1), (2), or (3); said pellet containing:

(a) the active agent, (b) said liquid pharmaceutically acceptable solubilizer for forming a liquid solution in which the active agent is dissolved, and (c) solid pharmaceutically acceptable particles on which said liquid solution is fixed, said solid particles containing said liquid solution being agglomerated in a system which is not a matrix or gel forming system containing matrix or gel forming components which can cause the pellet to gel in water or in gastric medium, said process comprising:

mixing together solid polymeric or inorganic particles and the active agent in powder form, mixing the so obtained mixture with the solubilizer, as the only solubilizer present, agglomerating the solid particles containing the liquid solution of active agent in the absence of said matrix and gel forming components to form an agglomerate which is not a matrix or gel, heat treating the agglomerate containing the liquid solution of active agent at a temperature between 40° C. and the boiling point of the solubilizer, and spheronizing the heat treated agglomerate, thereby forming pellets wherein the active ingredient is capable of substantially immediate release.

32. Process of claim 31, in which the active agent is dissolved in a solubilizer, the quantity of which is such that the weight ratio solubilizer/active agent is greater than 4.

33. Process of claim 31, in which the weight ratio solubilizer/particles is greater than 1:5.

34. Process of claim 31, in which the weight ratio solubilizer/particles is greater than 1:3.

35. Process of claim 31, in which the particles are heat treated at a temperature between 40° C. and 60° C.

36. Process of claim 31, in which after the agglomeration of the particles, the particles are heated at a temperature higher than 40° C. for at least 3 hours.

37. Process of claim 31, in which after the agglomeration of the particles, the particles are heated at a temperature of 40° C. to 60° C. for at least 3 hours.

38. Mixture of claim 21, in which the particles are selected from the group consisting of microcrystalline particles and water insoluble particles.

* * * * *